United States Patent [19]

York, Jr.

[11] Patent Number: 4,644,007

[45] Date of Patent: * Feb. 17, 1987

[54] 3-CHLORO-4-(4,5-DIHYDRO-1H-IMIDAZO-2-YL)-AMINO-5-ALKYLBENZOIC ACIDS, ESTERS, SALTS, COMPOSITIONS AND METHODS

[75] Inventor: Billie M. York, Jr., Fort Worth, Tex.

[73] Assignee: Alcon Laboratories, Inc., Fort Worth, Tex.

[*] Notice: The portion of the term of this patent subsequent to May 14, 2002 has been disclaimed.

[21] Appl. No.: 755,373

[22] Filed: Jul. 15, 1985

Related U.S. Application Data

[63] Continuation of Ser. No. 590,464, Mar. 16, 1984, abandoned, which is a continuation-in-part of Ser. No. 519,791, Aug. 3, 1983, Pat. No. 4,517,199, and Ser. No. 520,071, Aug. 3, 1983, Pat. No. 4,515,800, which is a continuation-in-part of Ser. No. 323,369, Nov. 20, 1981, abandoned.

[51] Int. Cl.$^4$ .................................... A61K 31/415
[52] U.S. Cl. .................................... 514/392; 514/913
[58] Field of Search .................................... 514/392, 913

[56] References Cited

U.S. PATENT DOCUMENTS

| | | |
|---|---|---|
| 2,938,038 | 5/1960 | Hirt .................................... 260/309.6 |
| 3,236,857 | 2/1966 | Zeik et al. .................................... 260/309.6 |
| 3,468,887 | 9/1969 | Stahle et al. .................................... 260/253 |
| 3,622,579 | 11/1971 | Stahle et al. .................................... 424/273 |
| 3,636,219 | 1/1972 | Culik et al. .................................... 424/265 |
| 3,872,121 | 3/1975 | Kummer et al. .................................... 424/273 |
| 3,931,216 | 1/1976 | Franzmairi .................................... 260/309.6 |
| 4,125,620 | 11/1978 | Stahle et al. .................................... 424/273 R |
| 4,166,859 | 9/1979 | Stahle et al. .................................... 424/273 R |
| 4,213,995 | 7/1980 | Stahle et al. .................................... 424/273 R |
| 4,250,186 | 2/1981 | Stahle et al. .................................... 424/273 R |
| 4,262,005 | 4/1981 | McCarthy .................................... 424/273 R |
| 4,287,201 | 9/1981 | Olson et al. .................................... 424/273 R |
| 4,293,564 | 10/1981 | Stahle et al. .................................... 424/273 R |

FOREIGN PATENT DOCUMENTS

| | | |
|---|---|---|
| 0035393 | 9/1981 | European Pat. Off. . |
| 0043659 | 1/1982 | European Pat. Off. . |
| 2831657 | 1/1980 | Fed. Rep. of Germany . |
| 2832310 | 7/1980 | Fed. Rep. of Germany . |
| 2905883 | 8/1980 | Fed. Rep. of Germany . |
| 2949287 | 11/1981 | Fed. Rep. of Germany . |
| 792696 | 6/1980 | South Africa . |
| 1180766 | 10/1967 | United Kingdom . |
| 1216945 | 12/1970 | United Kingdom . |
| 1279543 | 6/1972 | United Kingdom . |
| 1279931 | 6/1972 | United Kingdom . |
| 1595412 | 8/1981 | United Kingdom . |

OTHER PUBLICATIONS

DeJonge, Europ. J. of Pharm. 71 (1981) 411-420; "Discrimination Between Peripheral and Central Alpha-Adrenergic Effects Using Meta-Substituted Imidazolines".
J. Pharmcol. Methods 6(2) 109-20 (1981)-Stahle et al.
J. Labelled Compd. Radiopharm. 17(1), 35-41 (1980), Rouot et al.
J. Med. Chem. 24, 502-507 (1981)-Pieter et al.
Naunyn-Schmiedeberg's Pharmacol. 317(8), 1-12 (1981), DeJonge et al.
J. Auton. Pharmac. 1, 377-383 (1981)-DeJonge et al.
Brit. J. Pharmac. 71, 5-9 (1980)-Rouot et al.
CR Acad. Sci. Paris-286 (1978), Rouot et al.
Life Science 25, 769-774 (1979)-Rouot et al.
Invest. Ophthal. 17(2), 149-158 (1973), Krieglstein et al., "The Peripheral & Central Neural Action of Clonidine".
Chem. Abst. 92, 41944(d)-41946(f)-Stahle et al. (1980).

*Primary Examiner*—Douglas W. Robinson
*Attorney, Agent, or Firm*—Lowe, Price, LeBlanc, Becker & Shur

[57] ABSTRACT

3-chloro-4-(4,5-dihydro-1H-imidazao-2-yl)-amino-5-alkylbenzoic acid, its pharmaceutically acceptable metal salts and esters are useful in treating glaucoma by virtue of the effect in lowering intraocular pressure when administered systemically or topically to the eye. Also disclosed are processes for preparing the compounds, pharmaceutical compositions comprising the disclosed compounds; and methods of treatment comprising administering said compositions when a lowering of intraocular pressure is indicated.

14 Claims, No Drawings

3-CHLORO-4-(4,5-DIHYDRO-1H-IMIDAZO-2-YL)-AMINO-5-ALKYLBENZOIC ACIDS, ESTERS, SALTS, COMPOSITIONS AND METHODS

CROSS REFERENCE TO RELATED APPLICATIONS

This application is a continuation of Ser. No. 590,464, filed Mar. 16, 1984, now abandoned, which is a continuation-in-part of both Ser. No. 519,791, filed Aug. 3, 1983, now U.S. Pat. No. 4,517,199, and Ser. No. 520,071, filed Aug. 3, 1983, now U.S. Pat. No. 4,515,800, which are continuation-in-parts of Ser. No. 323,369, filed Nov. 20, 1981, now abandoned.

FIELD OF THE INVENTION

The present invention relates to certain substituted dihydro-1H-imidazoyl benzoic acids and esters which are useful in lowering intraocular pressure, and thus are useful in treating glaucoma.

BACKGROUND

Some medicaments presently available for treating glaucoma by lowering the intraocular pressure are not completely satisfactory because they are ineffective, and/or demonstrate unwanted cardio-vascular-pulmonary and CNS activities. Additionally, prior art compounds for this use plague the user with any one or more of the following side effects: obvious vasoconstricton or vasodilation of the vessels of the sclera; obvious pupil contraction or dilation; and painful stinging. Accordingly, there is a need in the art for compositions which are effective in lowering intraocular pressure and are devoid of unwanted side effects. Such freedom of side effects is particularly desired on topical administration to the eye.

SUMMARY OF THE INVENTION

It is accordingly one object of the invention to provide novel 3-chloro-4-(4,5-dihydro-1H-imidazo-2-yl)-amino-5-alkyl benzoic acids and esters, salts and methods of preparation.

A further object of the invention is to provide novel pharmaceutical compositions of matter containing these benzoic acids and esters as the effective ingredient, and methods for treating glaucoma by administration of these novel compositions.

Other objects and advantages of the present invention will become apparent as the description thereof proceeds.

In satisfaction of the foregoing objects and advantages, the present invention provides 3-chloro-4-(4,5-dihydro-1H-imidazo-2-yl)amino-5-alkylbenzoic acids, salts and the esters, which are useful in lowering intraocular pressure when administered topically or systemically to the eye and, thus, are useful in treating glaucoma; the novel compounds being of the following general formula:

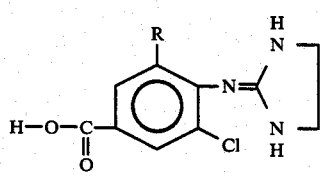

wherein R is methyl or ethyl and the pharmaceutically acceptable salts and esters thereof.

DESCRIPTION OF PREFERRED EMBODIMENTS

As indicated above, the present invention relates to novel substituted 4,5-dihydro-1H-imidazo-2-yl benzoic acids and derivatives. These compounds may be characterized by the following general formula:

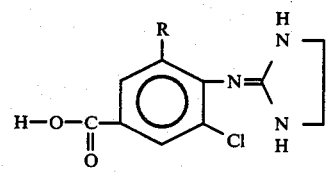

wherein R is methyl or ethyl and the pharmaceutically acceptable esters and salts thereof. The pharmaceutically acceptable acid addition salts from mineral acids or organic acids are also included with the scope of the invention.

The esters contemplated for the compounds of the invention include any ester moiety which permits the compound to retain its pharmaceutical use in lowering intraocular pressure, and provides a compound which is safe and effective. Thus the compounds covered by the above general formula include the free acid (—COOH), alkali and alkaline earth metal salts (e.g., Na, K, C₂, and Mg), and esters which may be illustrated by the functional group —COOR'. The invention is inclusive of all ester radicals, R', known to be effective as pharmaceutically acceptable esters. Lower alkyl esters are especially preferred. The pharmaceutically acceptable salts of the compounds of the present invention also include N-acid addition salts, such as the hydrochloride, hydrobromide, maleate, hydrogen sulfate, and the like.

As pointed out, the ester moiety may be any compatible group. More generally stated, pharmaceutically acceptable carboxyl derivatives of the present invention are those derived by reacting the free acid or salt derivative with alcohols, phenols, alkylating reagents and the like. For example, esters of interest from the above-listed starting materials are final products having the —COOR' group at the ester position, wherein R' is alkyl having 1–10 carbon atoms, straight or branched, such as methyl, ethyl, t-butyl, pentyl, decyl and the like; aminoalkyl including 2-methylaminoethyl, 2-diethylaminoethyl, 2-acetamidoethyl, phthalimidomethyl, succinimidomethyl; alkoxyalkyl wherein the alkoxy portion as 1–10 and preferably 1–6 carbon atoms; but can be branched, straight or cyclic, and the alkyl portion has 1–6 carbon atoms, such as methoxymethyl, ethoxymethyl, isopropoxymethyl, decyloxymethyl, ethoxymethyl, isopropoxymethyl, decyloxymethyl, ethoxypropyl, decyloxypentyl, cyclohexyloxymethyl and the like; alkanoloxyalkyl wherein the alkanoyloxy portion is straight or branched and has 1–6 carbon atoms and the alkyl portion has up to 16 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1–6 carbon atoms, e.e., 2,2,2-trichloroethyl, trifluoroethyl, 2-bromopropyl, diiodomethyl, 2-chloroethyl, 2-bromoethyl, and the like; alkenyl having 1–10 carbon atoms, either straight or branched, e.g., allyl, 2-propenyl, 3-butenyl, 4-butenyl, 4-pentenyl, 2-butenyl, 3-pentenyl, 3-methyl-3-butenyl, methallyl, 1,4-cyclohexadien-1-yl-methyl, and the like; alkynyl having 1–10 carbon atoms, either straight of branched, e.g., 3-pentynyl, propargyl, ethynyl, 3-butyn-1-yl, and the like; alkanoyl, either straight or branched, having 1–10 carbon atoms, such as pivaloyl, acetyl, propionyl, and the like, aralkyl or heteroaralkyl wherein alkyl has 1–3 carbon atoms, and hetero means 1–4 hetero-O-atoms, including benzyl, benzhydryl, and substituted benzyl and benzyhdryl, for e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as the cyclic analogues thereof, 2,2-dimethyl-5-coumaranmethyl, 5-indanylmethyl, p-trimethylsilybenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1–4 carbon atom chains); or phthalidyl; or phenylethyl, 2-(p-methylphenyl)ethyl, and the arylthioalkyl analogues, aryloxyalkyl wherein aryl is preferably a phenyl ring having 0–3 substituents, preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenylthiomethyl, phenylthioethyl; aryl and alkaryl wherein aryl is phenyl, naphthyl, 5-indanyl, or substituted phenyl having 0–3 substituents, preferably 0 or 1 substituent in the ortho or para position, e.g., (4-methyl)phenyl, (4-hydroxy)phenyl, (4-t-butyl)phenyl, p-nitrophenyl, 3,5-dinitrophenyl, or p-carboxyphenyl, the latter being either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)-benzyloxymethyl, (4-chloro)benzyloxymethyl; alkylthioalkyl wherein the alkylthio portion has 1–10 and preferably 1–6 carbon atoms, but can be branched, straight or cyclic, and the alkyl portion has 1–6 carbon atoms, such as methylthioethyl, ethylthioethyl, cyclohexylthiomethyl, decylthiobutyl, methylthiopropyl, isopropylthioethyl, methylthiobutyl and the like.

In the more preferred embodiment, R' is hydrogen, alkali metal, alkaline earth metal, straight or branch-chain lower alkyl, wherein the alkyl group has 1–6 carbon atoms, lower cycloalkyl, e.g., of 3–7 carbons such as cyclopropyl or cyclohexyl, lower cycloalkylalkyl of 4–8 carbons, e.g., cyclopropylmethyl, alkenyl of 2–7 carbons, e.g., propenyl, aryl of 5–13 carbons, e.g., phenyl, substituted aryl, e.g., anisolyl, such as those of the formula:

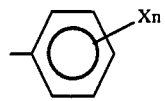

where X is halogen, methoxy, lower alkyl, e.g., methyl, and n is an integer of 1 to 5; or arylalkyl of 6–14 carbons, e.g., benzyl. The alkali metal may be Na, K or Li, and the alkaline earth metal may be Mg or Ca.

Preferred moieties for R' are methyl, ethyl, isopropyl, cyclopropyl, cyclopropylmethyl, cyclobutyl, isobutyl, and t-butyl.

It will be noted that the structural formula provided above is tautomeric in the double bond at the amino group attached to the imidazo-2-yl ring. The nomenclature set forth herein however is preferred.

The most preferred compounds within the scope of the invention include 3-chloro-4-(4,5-dihydro-1H-imidazo-2-yl)-amino-5-methyl benzoic acid and its ethyl ester.

The following compounds are also preferred:
3-chloro-4-(4,5-dihydro-1H-imidazo-2-yl)-amino-5-ethyl benzoic acid ethyl ester
3-chloro-4-(4,5-dihydro-1H-imidazo-2-yl)-amino-5-methyl benzoic acid isopropyl ester
3-chloro-4-(4,5-dihydro-1H-imidazo-2-yl)-amino-5-methyl benzoic acid cyclopropyl ester
3-chloro-4-(4,5-dihydro-1H-imidazo-2-yl)-amino-5-methyl benzoic acid t-butyl ester
3-chloro-4-(4,5-dihydro-1H-imidazo-2-yl)-amino-5-ethyl benzoic acid isopropyl ester.

The compounds of the present invention are useful in lowering intraocular pressure and thus are useful in the treatment of glaucoma. The compounds are essentially devoid of unwanted side effects such as vasoconstriction or vasodilation of the vessels of the sclera, pupil contraction or dilation, and painful stinging.

The compounds are preferably administered topically although other conventional methods may be used. In forming compositions for topical administration, the compounds are preferably formulated as 0.1 to 2.0 weight percent solutions in water at a pH of 4.5 to 8.0. While the precise regimen is left to the discretion of the clinician, it is recommended that the resulting solution be topically applied by placing one drop in each eye two times a day.

The compounds of the invention may be prepared from 1-acetyl imidazolidin-2-one and 4-amino-3-halo-5-alkylbenzonitrile by reaction in the presence of $POCl_3$ to produce 4-(1-acetyl-4,5-dihydro-1H-imidazo-2-yl)amino-3-halo-5-alkyl benzonitrile. This intermediate is then reacted with hydrochloric acid to effect deacetylation and remove the 1-acetyl group and also hydrolyze the nitrile group to carboxyl to form the free carboxylic acid. Alkali metal salts and alkaline earth metal salts of the acid may be formed conventionally. The acid or salt may be subsequently esterified with the appropriate alcohol, e.g., a $C_1$ to $C_5$ alkyl alcohol to yield the final ester products.

In a similar manner other carboxylic acid esterifications may be effected as is known in the art employing other lower alkyl, cycloalkyl, cycloalkylalkyl, aryl, or arylalkyl, alcohols such as isopropanol, cycloproanol, cyclopropylmethanol, phenyl, or benzyl alcohol, as exampled by the preparation of 3-chloro-4-(4,5-dihydro-1H-imidazo-2-yl)amino-5-methylbenzoic acid isopropyl ester prepared by the reaction of isopropanol and 3-chloro-4-(4,5-dihydro-1H-imidazo-2-yl)amino-5-methylbenzoic acid with the elimination of water. Since such esterification reactions are well known, they are not further described here. Acid addition salts of the final products may be formed by reaction with the appropriate mineral acid or organic acid by means known in the art.

The following examples are presented to illustrate the invention. In these examples and throughout the specification, parts are by weight unless otherwise indicated. Temperatures are in Celcius.

EXAMPLE 1

4-(1-ACETYL-4,5-DIHYDRO-1H—IMIDAZO-2-YL)-AMINO-3-CHLORO-5-METHYL BENZONITRILE

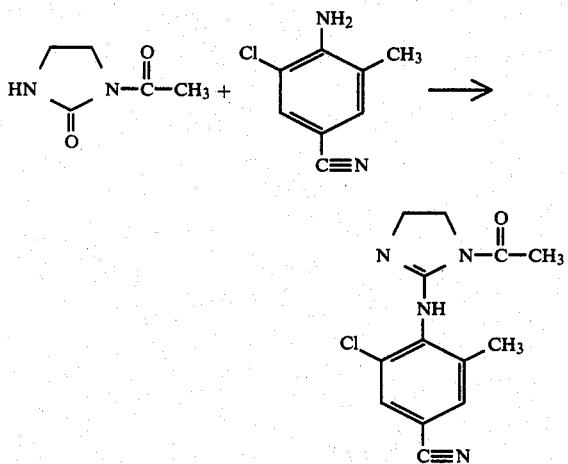

To a suspension at 1-acetyl imidazolidin-2-one (0.1 mole, 12.8 g) in phosphorous oxychloride (120 ml, 75° C.) was added 4-amino-3-chloro-5-methylbenzonitrile (0.1 mole, 16.6 g) in portions over a 45 minute period while maintaining the temperature at 75° C. The mixture was heated at 75°-80° C. for 18 hours and the phosphorous oxychloride was removed by evaporation in vacuo, the residue was poured onto ice (600 ml), the pH adjusted to 12 and the mixture extracted with chloroform. The combined extracts were dried (magnesium sulfate) and evaporated to a crude solid. An analytical sample was prepared by recrystallization from toluene: mp 184, 5°–186° C.; MS m/e 276 (m+).

Analysis. Calculated $C_{13}H_{13}ClN_4O$: C, 56.42; H, 4.73; N, 20.25. Found: C, 56.24; H, 4.76; N, 19.95.

EXAMPLE 2

3-CHLORO-4-(4,5-DIHYDRO-1H—IMIDAZO-2-YL)AMINO-5-METHYLBENZOIC ACID HYDROCHLORIDE

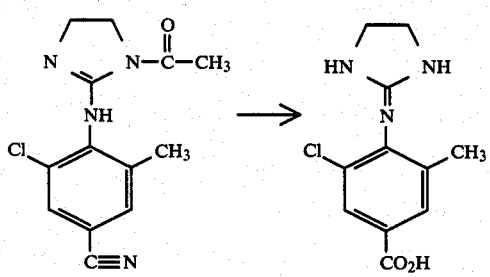

A suspension of 4-(1-acetyl-4,5-dihydro-1H-imidazo-2-yl)amino-3-chloro-5-methylbenzonitrile (28.9 m mole, 8.15 g) in 9N hydrochloric acid was heated at reflux temperature for 8 hours and cooled to room temperature. The solid was collected by filtration, washed with water and air dried. Recrystallization from methanol-ether gave 5.3 g of analytically pure material; mp 320° C.

Analysis. Calculated for $C_{11}H_{13}Cl_2N_3O_2$: C, 45.53; H, 4.52; N, 14.48. Found: C, 45.67; H, 4.65; N, 14.34.

EXAMPLE 3

3-CHLORO-4-(4,5-DIHYDRO-1H—IMIDAZO-2-YL)AMINO-5 METHYLBENZOIC ACID ETHYL ESTER

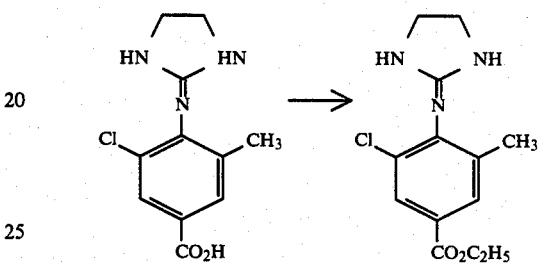

To a suspension of 3-chloro-4-(4,5-dihydro-1H-imidazo-2-yl)amino-5-methylbenzoic acid hydrochloride (8.6 m mole, 2.5 g) in ethanol (37 ml) at room temperature was added borontrifluoride etherate (20.3 m mole, 2.5 ml); this mixture was heated at reflux temperature for 16 hours. The reaction mixture was cooled (10° C.) and poured into a saturated aqueous solution of sodium bicarbonate (65 ml) and the pH of this mixture was adjusted to 9. The opaque solution was extracted with chloroform, the extracts were combined, dried, and evaporated to a solid. Recrystallization from acetonitrile provided 1.7 g of analytically pure material: mp 228°–229.5° C.; MS m/e 281 (m+).

Analysis. Calculated for $C_{13}H_{16}ClN_3O_2$: C, 55.42; H, 5.73; N, 14.91. Found: C, 55.29; H, 5.80; N, 14.78.

EXAMPLES 4–8

Using the general esterification procedure and starting benzoic acid salt starting material of Example 3, the following esters are prepared using the indicated alcohol

EXAMPLE 4

Esterification with ethyl alcohol: 3-chloro-4-(4,5-dihydro-1H-imidazo-2-yl)-amino-5-ethyl benzoic acid ethyl ester.

EXAMPLE 5

Esterification with isopropyl alcohol: 3-chloro-4-(4,5-dihydro-1H-imidazo-2-yl)-amino-5-methyl benzoic acid isopropyl ester.

EXAMPLE 6

Esterification with cyclopropanol: 3-chloro-4-(4,5-dihydro-1H-imidazo-2-yl)-amino-5-methyl benzoic acid cyclopropyl ester.

EXAMPLE 7

Esterification with t-butyl alcohol: 3-chloro-4-(4,5-dihydro-1H-imidazo-2-yl)-amino-5-methyl benzoic acid t-butyl ester.

EXAMPLE 8

Esterification with cyclopropyl methanol: 3-chloro-4-(4,5-dihydro-1H-imidazo-2-yl)-amino-5-ethyl benzoic acid cyclopropyl methyl ester.

EXAMPLE 9

The following are representative pharmaceutical compositions of the preferred compound of Example 3 of the invention for topical use in lowering of intraocular pressure.

| COMPOSITION A | |
|---|---|
| Ingredient | Percentage by Weight |
| 1.0% w/v of the compound of Example 3 | 1.0 |
| Benzalkonium chloride | 0.01 |
| Sodium acetate | 0.07 |
| Sodium chloride | 0.6 |
| Hydrochloric acid and/or sodium hydroxide | to adjust pH to 5.0 to 5.5 |
| Purified Water | q.s. to 100% |

| COMPOSITION B | |
|---|---|
| Ingredient | Percentage by Weight |
| 1.5% w/v of the compound of Example 3 | 1.5 |
| Benzalkonium chloride | 0.01 |
| Dried sodium phosphate | 0.01 |
| Sodium biphosphate | 0.07 |
| Sodium chloride | 0.18 |
| Sodium hydroxide and/or hydrochloric acid | to adjust pH |
| Purified Water | q.s. to 100% |

| COMPOSITION C | |
|---|---|
| Ingredient | Percentage by Weight |
| 0.5% w/v of the compound of Example 3 | 0.5 |
| Benzalkonium chloride | 0.01 |
| Sodium acetate | 0.14 |
| Disodium edetate | 0.01 |
| Sodium chloride | 0.52 |
| Hydrochloric acid and/or sodium hydroxide | to adjust pH |
| Hydroxypropylmethylcellulose | 0.5 |
| Purified Water | q.s to 100% |

The invention has been described herein by reference to certain preferred embodiments. However, as obvious variations thereon will become apparent to those skilled in the art, the invention is not to be considered as limited thereto.

What is claimed is:

1. An ophthalmic pharmaceutical composition comprising an intraocular pressure lowering amount of a compound of the following general formula:

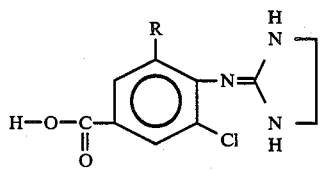

wherein R is methyl or ethyl, and the pharmaceutically acceptable salts and esters thereof, and a pharmaceutically acceptable vehicle therefor.

2. An ophthalmic pharmaceutical composition according to claim 1 wherein the compound is of the following general formula:

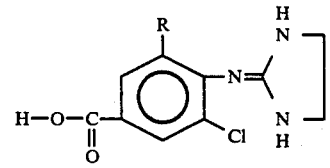

wherein R is methyl or ethyl, the alkali metal salts, the alkaline earth metal salts, the pharmaceutically acceptable esters and the pharmaceutically acceptable acid addition salts thereof, wherein said esters are esters of the —COOH group wherein the ester is of the formula —COOR', wherein R' is selected from the group consisting of lower alkyl of up to 6 carbon atoms, lower cycloalkyl of 3 to 7 carbon atoms, lower cycloalkylalkyl of 4 to 8 carbon atoms, alkynyl of 2 to 7 carbon atoms, aryl of 5 to 13 carbon atoms, including aryl substituted by up to 5 substituents selected from the group consisting of halogen, methoxy, and lower alkyl; and arylalkyl of 6 to 14 carbon atoms.

3. A composition according to claim 2 wherein the compound is of the following formula:

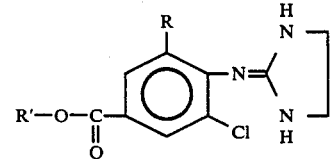

wherein R is methyl or ethyl, R' is hydrogen, alkali metal, methyl, ethyl, isopropyl, n-propyl, t-butyl, cyclopropyl, or cyclopropylmethyl and the pharmaceutically acceptable acid addition salts thereof.

4. A composition according to claim 2 wherein the compound is of the following formula:

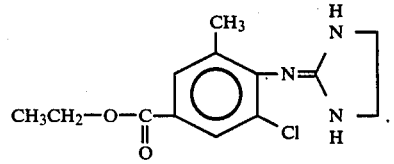

5. A composition according to claim 2 wherein the compound is of the following formula:

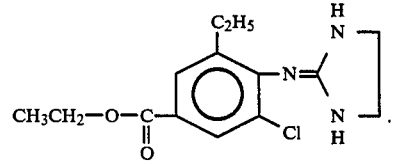

6. A composition according to claim 2 wherein the compound is of the following formula:

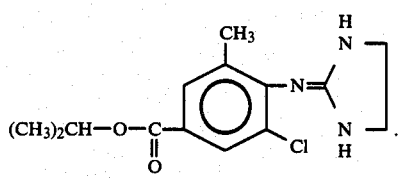

7. A composition according to claim 2 wherein the compound is of the following formula:

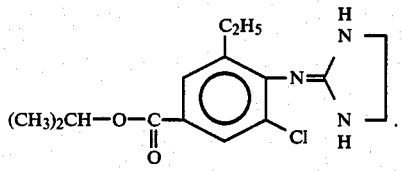

8. A composition according to claim 2 wherein the compound is of the following formula:

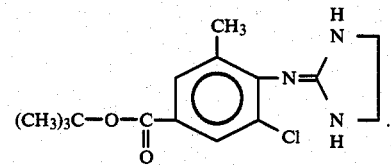

9. A composition according to claim 2 wherein the compound is of the following formula:

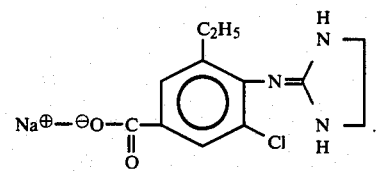

10. A composition according to claim 2 wherein the compound is of the following formula:

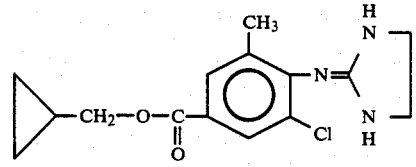

11. A composition according to claim 1 wherein the compound is present in the vehicle in an amount of 0.1 to 2.0 wt.% and at a pH of 4.5 to 8.0.

12. A method of lowering intraocular pressure comprising administering to the eye a therapeutically effective amount of a composition of claim 1.

13. A method of lowering intraocular pressure comprising administering to the eye a therapeutically effective amount of a composition of claim 2.

14. A method of lowering intraocular pressure according to claim 12 wherein the composition is administered topically.

* * * * *